United States Patent
Cheon et al.

(10) Patent No.: US 6,951,952 B2
(45) Date of Patent: Oct. 4, 2005

(54) DYES

(75) Inventors: Kap-Soo Cheon, Shrewsbury, MA (US); Michael P. Filosa, Medfield, MA (US); Stephen J. Telfer, Arlington, MA (US)

(73) Assignee: Polaroid Corporation, Waltham, MA (US)

( * ) Notice: Subject to any disclaimer, the term of this patent is extended or adjusted under 35 U.S.C. 154(b) by 2 days.

(21) Appl. No.: 10/789,276

(22) Filed: Feb. 27, 2004

(65) Prior Publication Data

US 2004/0176617 A1 Sep. 9, 2004

Related U.S. Application Data

(60) Provisional application No. 60/451,208, filed on Feb. 28, 2003.

(51) Int. Cl.⁷ ............... C07D 307/94; C07D 405/14; C07D 493/10
(52) U.S. Cl. .................. 549/265; 546/282.7
(58) Field of Search ............. 549/265; 546/282.7

(56) References Cited

U.S. PATENT DOCUMENTS

| | | | |
|---|---|---|---|
| 4,544,936 A | 10/1985 | Yokoi | 346/209 |
| 5,395,948 A | 3/1995 | Zink | 549/225 |
| 6,054,246 A | 4/2000 | Bhatt et al. | 430/151 |
| 6,162,931 A | 12/2000 | Gee et al. | 549/223 |
| 6,229,055 B1 | 5/2001 | Klaubert et al. | 568/765 |
| 6,537,410 B2 | 3/2003 | Arnost et al. | 156/235 |

FOREIGN PATENT DOCUMENTS

| | | | |
|---|---|---|---|
| DE | 96668 | 3/1898 | |
| EP | 0 107 780 A2 | 5/1984 | ......... C07D/493/10 |
| JP | 59062666 | 4/1984 | ........... C09B/11/28 |
| JP | 07076587 | 3/1995 | ......... C07D/493/10 |

OTHER PUBLICATIONS

U.S. Appl. No. 10/789,648, filed Feb. 27, 2004, Chu et al.
U.S. Appl. No. 10/789,600, filed Feb. 27, 2004, Allen et al.
U.S. Appl. No. 10/151,432, filed May 20, 2002, Bhatt et al.

*Primary Examiner*—Taofiq Solola

(57) ABSTRACT

There are described novel rhodol dye compounds The dye compounds exhibit a first color when in the crystalline form and a second color, different from the first color, when in the liquid, amorphous form.

4 Claims, No Drawings

DYES

REFERENCE TO RELATED APPLICATIONS

This application claims the benefit of provisional application Ser. No. 60/451,208, filed Feb. 28, 2003.

This application is related to the following commonly assigned United States patent applications and patents, the disclosures of all of which are hereby incorporated by reference herein in their entirety:

U.S. patent application Ser. No. 10/789,648, filed on even date herewith;

U.S. patent application Ser. No. 10/789,600, filed on even date herewith;

U.S. patent application Ser. No. 6,537,410B2

U.S. patent application Ser. No. 10/151,432 filed May 20, 2002 (United States Patent Application Publication No. US2003/0125206 A1); and U.S. patent application Ser. No. 6,054,246.

U.S. patent application Ser. No. 10/151,432, filed May 20, 2002 (U.S. Patent Application No. US2003/0125206 A1) now U.S. Pat. No. 6,801,233 B2; and U.S. Pat. No. 6,054,246.

FIELD OF THE INVENTION

This invention relates to novel compounds and, more particularly, to compounds which exhibit one color in a first tautomeric form and a second, different color in a second tautomeric form.

BACKGROUND OF THE INVENTION

The development of thermal print heads (linear arrays of individually-addressable resistors) has led to the development of a wide variety of thermally-sensitive media. In some of these, known as "thermal transfer" systems, heat is used to move colored material from a donor sheet to a receiver sheet. Alternatively, heat may be used to convert a colorless coating on a single sheet into a colored image, in a process known as "direct thermal" imaging. Direct thermal imaging has the advantage over thermal transfer of the simplicity of a single sheet. On the other hand, unless a fixing step is incorporated, direct thermal systems are still sensitive to heat after thermal printing. If a stable image is needed from an unfixed direct thermal system, the temperature for coloration must be higher than any temperature that the image is likely to encounter during normal use. A problem arises in that the higher the temperature for coloration, the less sensitive the medium will be when printed with the thermal print head. High sensitivity is important for maximum speed of printing, for maximizing the longevity of the print head, and for energy conservation in mobile, battery-powered printers. As described in more detail below, maximizing sensitivity while maintaining stability is more easily achieved if the temperature of coloration of a direct thermal medium is substantially independent of the heating time.

Thermal print heads address one line of the image at a time. For reasonable printing times, each line of the image is heated for about ten milliseconds or less. Storage of the medium (prior to printing or in the form of the final image) may need to be for years, however. Thus, for high imaging sensitivity, a high degree of coloration is required in a short time of heating, while for good stability a low degree of coloration is required for a long time of heating.

Most chemical reactions speed up with increasing temperature. Therefore, the temperature required for coloration in the short heating time available from a thermal print head will normally be higher than the temperature needed to cause coloration during the long storage time. Actually reversing this order of temperatures would be a very difficult task, but maintaining a substantially time-independent temperature of coloration, such that both long-time and short-time temperatures for coloration are substantially the same, is a desirable goal that is achieved by the present invention.

There are other reasons why a time-independent coloration temperature may be desirable. It may, for example, be required to perform a second thermal step, requiring a relatively long time of heating, after printing. An example of such a step would be thermal lamination of an image. The temperature of coloration of the medium during the time required for thermal lamination must be higher than the lamination temperature (otherwise the medium would become colorized during lamination). It would be preferred that the imaging temperature be higher than the lamination temperature by as small a margin as possible, as would be the case for time-independent temperature of coloration.

Finally, the imaging system may comprise more than one color-forming layer and be designed to be printed with a single thermal print-head, as described in the above-mentioned patent application Ser. No. 10/151,432. In one embodiment of the imaging system, the topmost color-forming layer forms color in a relatively short time at a relatively high temperature, while the lower layer or layers form color in a relatively long time at a relatively low temperature. An ideal topmost layer for this type of direct thermal imaging system would have time-independent temperature of coloration.

Prior art direct thermal imaging systems have used several different chemical mechanisms to produce a change in color. Some have employed compounds that are intrinsically unstable, and which decompose to form a visible color when heated. Such color changes may involve a unimolecular chemical reaction. This reaction may cause color to be formed from a colorless precursor, the color of a colored material to change, or a colored material to bleach. The rate of the reaction is accelerated by heat. For example, U.S. Pat. No. 3,488,705 discloses thermally unstable organic acid salts of triarylmethane dyes that are decomposed and bleached upon heating. U.S. Pat. No. 3,745,009 reissued as U.S. Reissue Pat. No. 29,168 and U.S. Pat. No. 3,832,212 disclose heat-sensitive compounds for thermography containing a heterocyclic nitrogen atom substituted with an —OR group, for example, a carbonate group, that decolorize by undergoing homolytic or heterolytic cleavage of the nitrogen-oxygen bond upon heating to produce an RO+ ion or RO' radical and a dye base or dye radical which may in part fragment further. U.S. Pat. No. 4,380,629 discloses styryl-like compounds that undergo coloration or bleaching, reversibly or irreversibly, via ring-opening and ring-closing in response to activating energies. U.S. Pat. No. 4,720,449 describes an intramolecular acylation reaction that converts a colorless molecule to a colored form. U.S. Pat. No. 4,243,052 describes pyrolysis of a mixed carbonate of a quinophthalone precursor that may be used to form a dye. U.S. Pat. No. 4,602,263 describes a thermally-removable protecting group that may be used to reveal a dye or to change the color of a dye. U.S. Pat. No. 5,350,870 describes an intramolecular acylation reaction that may be used to induce a color change. A further example of a unimolecular color-forming reaction is described in "New Thermo-Response Dyes: Coloration by the Claisen Rearrangement and Intramolecular Acid-Base Reaction Masahiko Inouye, Kikuo Tsuchiya, and Teijiro Kitao, Angew. Chem. Int. Ed. Engl. 31, pp. 204–5 (1992).

In all of the above-mentioned examples, control of the chemical reaction is achieved through the change in rate that occurs with changing temperature. Thermally-induced changes in rates of chemical reactions in the absence of phase changes may often be approximated by the Arrhenius equation, in which the rate constant increases exponentially as the reciprocal of absolute temperature decreases (i.e., as temperature increases). The slope of the straight line relating the logarithm of the rate constant to the reciprocal of the absolute temperature is proportional to the so-called "activation energy". The prior art compounds described above are coated in an amorphous state prior to imaging, and thus no change in phase is expected or described as occurring between room temperature and the imaging temperature. Thus, as employed in the prior art, these compounds exhibit strongly time-dependent coloration temperatures. Some of these prior art compounds are described as having been isolated in crystalline form. Nevertheless, in no case is there mentioned in this prior art any change in activation energy of the color-forming reaction that may occur when crystals of the compounds are melted.

Other prior art thermal imaging media depend upon melting to trigger image formation. Typically, two or more chemical compounds that react together to produce a color change are coated onto a substrate in such a way that they are segregated from one another, for example, as dispersions of small crystals. Melting, either of the compounds themselves or of an additional fusible vehicle, brings them into contact with one another and causes a visible image to be formed. For example, a colorless dye precursor may form color upon heat-induced contact with a reagent. This reagent may be a Bronsted acid, as described in "Imaging Processes and Materials", Neblette's Eighth Edition, J. Sturge, V. Walworth, A. Shepp, Eds., Van Nostrand Reinhold, 1989, pp. 274–275, or a Lewis acid, as described for example in U.S. Pat. No. 4,636,819. Suitable dye precursors for use with acidic reagents are described, for example, in U.S. Pat. No. 2,417,897, South African Patent 68-00170, South African Patent 68-00323 and Ger. Offenlegungschrift 2,259,409. Further examples of such dyes may be found in "Synthesis and Properties of Phthalide-type Color Formers", by Ina Fletcher and Rudolf Zink, in "Chemistry and Applications of Leuco Dyes", Muthyala Ed., Plenum Press, New York, 1997. The acidic material may for example be a phenol derivative or an aromatic carboxylic acid derivative. Such thermal imaging materials and various combinations thereof are now well known, and various methods of preparing heat-sensitive recording elements employing these materials also are well known and have been described, for example, in U.S. Pat. Nos. 3,539,375, 4,401,717 and 4,415,633.

Prior art systems in which at least two separate components are mixed following a melting transition suffer from the drawback that the temperature required to form an image in a very short time by a thermal print-head may be substantially higher than the temperature required to colorize the medium during longer periods of heating. This difference is caused by the change in the rate of the diffusion needed to mix the molten components together, which may become limiting when heat is applied for very short periods. The temperature may need to be raised well above the melting points of the individual components to overcome this slow rate of diffusion. Diffusion rates may not be limiting during long periods of heating, however, and the temperature at which coloration takes place in these cases may actually be less than the melting point of either individual component, occurring at the eutectic melting point of the mixture of crystalline materials.

As the state of the art in imaging systems advances and efforts are made to provide new imaging systems that can meet new performance requirements, and to reduce or eliminate some of the undesirable characteristics of the known systems, it would be advantageous to have new dye compounds which can be used in imaging systems, including thermal imaging systems.

SUMMARY OF THE INVENTION

It is therefore an object of this invention to provide novel compounds.

Another object of the invention is to provide compounds having different tautomeric forms that exhibit different colors.

Yet another object of the invention is to provide novel compounds which may be used in conjunction with complexing agents to form complexes which are useful in imaging systems, including thermal imaging systems.

The present invention provides novel rhodol compounds that are useful in the preparation of compounds which can be used as image dyes in imaging systems. According to one aspect of the invention there are provided novel dye compounds which exhibit a first color when crystallized together with a complexing agent and a second color, different from the first color, when in the liquid, amorphous form together with the same complexing agent.

In one embodiment of the invention there are provided novel compounds of which the colorless tautomeric form is represented by formula I

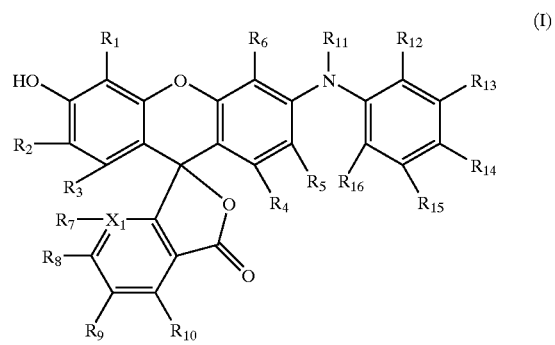

wherein
$R_1$, $R_2$, $R_3$, $R_4$, $R_5$ and $R_6$ are each independently selected from the group consisting of hydrogen, alkyl, preferably having from 1 to 18 carbon atoms, substituted alkyl, alkenyl, substituted alkenyl, alkynyl, substituted alkynyl, heterocycloalkyl, substituted heterocycloalkyl, substituted carbonyl, acylamino, halogen, nitro, nitrilo, sulfonyl, aryl, substituted aryl, heteroaryl, substituted heteroaryl, oxygen, substituted oxygen, nitrogen, substituted nitrogen, sulfur and substituted sulfur;

$R_7$ is absent or selected from the group consisting of hydrogen, alkyl, preferably having from 1 to 18 carbon atoms, substituted alkyl, alkenyl, substituted alkenyl, alkynyl, substituted alkynyl, heterocycloalkyl, substituted heterocycloalkyl, substituted carbonyl, acylamino, halogen, nitro, nitrilo, sulfonyl, aryl, substituted aryl, heteroaryl, substituted heteroaryl, oxygen, substituted oxygen, nitrogen, substituted nitrogen, sulfur and substituted sulfur;

$R_8$, $R_9$, $R_{10}$, $R_{13}$, $R_{14}$, $R_{15}$ and $R_{16}$ are each independently selected from the group consisting of hydrogen, alkyl, preferably having from 1 to 18 carbon atoms, substituted alkyl, alkenyl, substituted alkenyl, alkynyl, substituted alkynyl, heterocycloalkyl, substituted heterocycloalkyl, substituted carbonyl, acylamino, halogen, nitro, nitrilo, sulfonyl, aryl, substituted aryl, heteroaryl, substituted heteroaryl, oxygen, substituted oxygen, nitrogen, substituted nitrogen, sulfur and substituted sulfur;

$R_{11}$ is selected from the group consisting of hydrogen, alkyl, preferably having from 1 to 18 carbon atoms, substituted alkyl, alkenyl, substituted alkenyl, alkynyl, substituted alkynyl, heterocycloalkyl, substituted heterocycloalkyl, substituted carbonyl, sulfonyl, aryl, substituted aryl, heteroaryl, substituted heteroaryl, substituted oxygen and substituted nitrogen;

$R_{12}$ is selected from the group consisting of hydrogen, alkyl, preferably having from 1 to 18 carbon atoms, substituted alkyl, alkenyl, substituted alkenyl, alkynyl, substituted alkynyl, heterocycloalkyl, substituted heterocycloalkyl, substituted carbonyl, acylamino, halogen, nitro, nitrilo, sulfonyl, aryl, substituted aryl, heteroaryl, substituted heteroaryl, oxygen, substituted oxygen, nitrogen, substituted nitrogen, sulfur and substituted sulfur;

or $R_{11}$ and $R_{12}$ taken together represent the carbon atoms necessary to form a 5 or 6 membered substituted or unsubstituted heterocycloalkyl or heteroaryl group; and $X_1$ is carbon or nitrogen.

In a preferred group of dyes according to the invention $R_2$ is an electron-withdrawing group such as bromine or sulfonamide and $R_{11}$ is hydrogen, alkyl, preferably having from 1 to 12 carbon atoms, substituted alkyl, or aryl such as phenyl and substituted phenyl, $R_1$, $R_3$, $R_4$, $R_5$, $R_6$, $R_7$, $R_8$, $R_9$, $R_{10}$ $R_{12}$, $R_{13}$, $R_{14}$, $R_{15}$ and $R_{16}$ are each hydrogen and $X_1$ is carbon.

In another preferred group of compounds according to the invention $R_2$ is hydrogen or alkyl, preferably having from 1 to 12 carbon atoms, $R_7$, $R_8$, $R_9$ and $R_{10}$ are halogen, $R_{11}$ is hydrogen, alkyl, preferably having from 1 to 12 carbon atoms, substituted alkyl, aryl such as phenyl and substituted phenyl, or substituted aryl, $R_1$, $R_3$, $R_4$, $R_5$, $R_6$, $R_{12}$, $R_{13}$, $R_{14}$, $R_{15}$ and $R_{16}$ are each hydrogen and $X_1$ is carbon.

In yet another preferred group of compounds according to the invention $R_2$ is hydrogen or alkyl, preferably having from 1 to 12 carbon atoms, $R_7$, $R_8$, $R_9$ and $R_{10}$ are hydrogen or halogen, $R_1$, $R_3$, $R_4$, $R_5$, $R_6$, $R_{13}$, $R_{14}$, $R_{15}$ and $R_{16}$ are each hydrogen, $X_1$ is carbon, and $R_{11}$ and $R_{12}$, taken together, form a saturated ring, e.g., indoline or tetrahydroquinoline.

As mentioned above, the compounds of the present invention exhibit at least two tautomeric forms, at least one of which is substantially colorless and represented by the structure shown in formula I, and at least another of which is colored. In practice, it is not straightforward to prepare colorless crystals of the compounds of the present invention in their pure form, although it is possible to observe the colorless tautomeric form in solution in certain solvents, for example, acetone. Colorless crystals of the compounds of the present invention can be prepared by use of a complexing agent, as described in commonly assigned U.S. patent application, Ser. No.10/789,600, filed on even date herewith, the entire disclosure of which is incorporated by reference herein and made part of this application.

Melting or dissolving colorless crystals prepared from compounds of the present invention and a complexing agent results in formation of an amorphous form in which some of the colored tautomeric form of the compound is present, giving rise to a visible change of color.

The conversion to the liquid or amorphous form can be carried out by applying heat to the crystals derived from the compounds and a complexing agent and therefore the compounds are useful in thermal imaging members used in thermal imaging methods. In such thermal imaging methods thermal energy may be applied to the thermal imaging members by any of the techniques known in thermal imaging such as from a thermal print head, a laser, a heated stylus, etc. In another embodiment, the conversion to the liquid form may be effected by applying a solvent for the crystalline solid such as from an ink jet imaging apparatus to at least partially dissolve the crystalline material. In another embodiment, one or more thermal solvents, which are crystalline materials, can be incorporated in the thermal imaging member. The crystalline thermal solvent(s), upon being heated, melt and dissolve or liquefy, and thereby convert, at least partially, the crystalline image-forming material to the liquid amorphous form to form the image.

Complexes formed from the compounds of the invention may be incorporated in any suitable imaging members including thermal imaging members. Typical suitable thermal imaging members generally comprise a substrate carrying at least one image-forming layer including a compound in the crystalline form, which can be converted, at least partially to a liquid in the amorphous form, the liquid having intrinsically a different color from the crystalline form. The thermal imaging member may be monochrome or multicolor and the temperature at which an image is formed in at least one of the image-forming layers is time independent.

Preferred thermal imaging members are those having the structures described in prior co-pending commonly assigned U.S. patent application Ser. No. 09/745,700 filed Dec. 20, 2000, now U.S. Pat. No. 6,537,410 B1 which is hereby incorporated herein by reference in its entirety and made a part of this application.

Other preferred thermal imaging members are those having the structures described in prior, co-pending commonly assigned U.S. patent application Ser. No. 10/151,432 filed May 20, 2002 which is hereby incorporated herein by reference in its entirety and made a part of this application.

Further preferred thermal imaging members are those having the structures described in U.S. Pat. No. 6,054,246 which is hereby incorporated herein by reference in its entirety and made a part of this application.

DETAILED DESCRIPTION OF THE INVENTION

A first embodiment of the invention is a compound represented by Formula I as described above.

Representative compounds according to the invention are those represented by formula I in which $R_1$, $R_3$, $R_4$, $R_5$, $R_6$, $R_{13}$, $R_{14}$, $R_{15}$ and $R_{16}$ are each hydrogen, $X_1$ is carbon, and the other substituents are as shown in Table I:

TABLE I

| Compound | $R_2$ | $R_7$ | $R_8$ | $R_9$ | $R_{10}$ | $R_{11}$ | $R_{12}$ |
|---|---|---|---|---|---|---|---|
| I | Br | H | H | H | H | H | H |
| II | Br | H | H | H | H | $C_{12}H_{25}$ | H |
| III | $C_6H_{13}$ | Cl | Cl | Cl | Cl | $C_6H_5$ | H |
| IV | $C_6H_{13}$ | Cl | Cl | Cl | Cl | 2-methyl-1-butyl | H |
| V | $C_6H_{13}$ | Cl | Cl | Cl | Cl | $C_{12}H_{25}$ | H |

TABLE I-continued

| Compound | $R_2$ | $R_7$ | $R_8$ | $R_9$ | $R_{10}$ | $R_{11}$ | $R_{12}$ |
|---|---|---|---|---|---|---|---|
| VI | $C_6H_{13}$ | Cl | Cl | Cl | Cl | 2-ethyl-1-hexyl | H |
| VII | H | H | H | H | H | R11 + R12 = CH$_2$CH$_2$ | — |

Definitions

The term "alkyl" as used herein refers to saturated straight-chain, branched-chain or cyclic hydrocarbon radicals. Examples of alkyl radicals include, but are not limited to, methyl, ethyl, propyl, isopropyl, n-butyl, tert-butyl, neopentyl, n-hexyl, cyclohexyl, n-octyl, n-decyl, n-dodecyl and n-hexadecyl radicals.

The term "alkenyl" as used herein refers to unsaturated straight-chain, branched-chain or cyclic hydrocarbon radicals. Examples of alkenyl radicals include, but are not limited to, allyl, butenyl, hexenyl and cyclohexenyl radicals.

The term "alkynyl" as used herein refers to unsaturated hydrocarbon radicals having at least one carbon-carbon triple bond. Representative alkynyl groups include, but are not limited to, ethynyl, 1-propynyl, 1-butynyl, isopentynyl, 1,3-hexadiynyl, n-hexynyl, 3-pentynyl, 1-hexen-3-ynyl and the like.

The terms "halo" and "halogen," as used herein, refer to an atom selected from fluorine, chlorine, bromine and iodine.

The term "aryl," as used herein, refers to a mono-, bicyclic or tricyclic carbocyclic ring system having one, two or three aromatic rings including, but not limited to, phenyl, naphthyl, anthryl, azulyl, tetrahydronaphthyl, indanyl, indenyl and the like.

The term "heteroaryl," as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

The term "heterocycloalkyl," as used herein, refers to a non-aromatic 3-, 4-, 5-, 6- or 7-membered ring or a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "carbonyl" as used herein refers to a carbonyl group, attached to the parent molecular moiety through the carbon atom, this carbon atom also bearing a hydrogen atom, or in the case of a "substituted carbonyl" a substituent as described in the definition of "substituted" below.

The term "acyl" as used herein refers to groups containing a carbonyl moiety. Examples of acyl radicals include, but are not limited to, formyl, acetyl, propionyl, benzoyl and naphthyl.

The term "alkoxy", as used herein, refers to a substituted or unsubstituted alkyl, alkenyl or heterocycloalkyl group, as previously defined, attached to the parent molecular moiety through an oxygen atom. Examples of alkoxy radicals include, but are not limited to, methoxy, ethoxy, propoxy, isopropoxy, n-butoxy, tert-butoxy, neopentoxy and n-hexoxy.

The term "aryloxy" as used herein refers to a substituted or unsubstituted aryl or heteroaryl group, as previously defined, attached to the parent molecular moiety through an oxygen atom. Examples of aryloxy include, but are not limited to, phenoxy, p-methylphenoxy, naphthoxy and the like.

The term "alkylamino", as used herein, refers to a substituted or unsubstituted alkyl, alkenyl or heterocycloalkyl group, as previously defined, attached to the parent molecular moiety through a nitrogen atom. Examples of alkylamino radicals include, but are not limited to, methylamino, ethylamino, hexylaminoand dodecylamino.

The term "arylamino", as used herein, refers to a substituted or unsubstituted aryl or heteroaryl group, as previously defined, attached to the parent molecular moiety through a nitrogen atom.

The term "substituted" as used herein in phrases such as "substituted alkyl", "substituted alkenyl", "substituted aryl", "substituted heteroaryl", "substituted heterocycloalkyl", "substituted carbonyl", "substituted alkoxy", "substituted acyl", "substituted amino", "substituted aryloxy", and the like, refers to independent replacement of one or more of the hydrogen atoms on the substituted moiety with substituents independently selected from, but not limited to, alkyl, alkenyl, heterocycloalkyl, alkoxy, aryloxy, hydroxy, amino, alkylamino, arylamino, cyano, halo, mercapto, nitro, carbonyl, acyl, aryl and heteroaryl groups.

The colored and colorless tautomeric forms of the molecules of the present invention must meet certain criteria for image quality and permanence. The colorless form, which as described above is preferably in combination with a complexing agent in the crystalline form, should have minimal visible absorption. It should be stable to light, heating below the melting point, humidity, and other environmental factors such as ozone, oxygen, nitrogen oxides, fingerprint oils, etc. These environmental factors are well known to those skilled in the imaging art. The colored form, present in the amorphous state, should be stable also to the above mentioned conditions, and in addition should not recrystallize to the colorless form under normal handling conditions of the image. The colored form should have a spectral absorption appropriate for digital color rendition. Typically, the colored form should be yellow (blue-absorbing), magenta (green-absorbing), cyan (red absorbing), or black, without undue absorption in an unintended spectral region. For nonphotographic applications, however, it may be required that the colored form not be one of the subtractive primary colors, but rather a particular spot color (for example, orange, blue, etc.). The preferred compounds of the present invention are designed to give a magenta coloration.

The thermal imaging members can be direct thermal imaging members wherein an image is formed in the member itself or they can be thermal transfer imaging members whereby image-forming material is transferred to an image-receiving member. The melting point of crystals (formed from molecules of the present invention with complexing agents) used in direct thermal imaging members of the present invention is preferably in the range of about 60° C. to about 300° C. Melting points lower than about 60° C. lead to direct thermal imaging members that are unstable to temperatures occasionally encountered during handling of the members before or after imaging, while melting temperatures above about 300° C. render the compounds difficult to colorize with a conventional thermal print head. It should be noted, however, that there are uses for certain novel compounds of the present invention that do not require the use of thermal print heads (for example, laser imaging).

To form a direct thermal imaging system, the crystalline, colorless form of the compounds of the invention with a complexing agent is made into a dispersion in a solvent in which the crystals are insoluble or only sparingly soluble, by any of the methods known in the art for forming dispersions. Such methods include grinding, attriting, etc. The particular solvent chosen will depend upon the particular crystalline material. Solvents that may be used include water, organic solvents such as hydrocarbons, esters, alcohols, ketones, nitrites, and organic halide solvents such as chlorinated and fluorinated hydrocarbons. The dispersed crystalline material may be combined with a binder, which may be polymeric. Suitable binders include water-soluble polymers such as poly(vinyl alcohol), poly(vinylpyrollidone) and cellulose derivatives, water-dispersed latices such as styrene/butadiene or poly(urethane) derivatives, or alternatively hydrocarbon-soluble polymers such as polyethylene, polypropylene, copolymers of ethylene and norbornene, and polystyrene. This list is not intended to be exhaustive, but is merely intended to indicate the breadth of choice available for the polymeric binder. The binder may be dissolved or dispersed in the solvent.

Following preparation of the dispersion of the compound of the present invention, and optional addition of a polymeric binder, the resultant fluid is coated onto a substrate using any of the techniques well-known in the coating art. These include slot, gravure, Mayer rod, roll, cascade, spray, and curtain coating techniques. The image-forming layer so formed is optionally overcoated with a protective layer or layers.

Where complexes of compounds of the present invention are used to prepare an imaging medium of the type described in copending U.S. patent application Ser. No. 10/151,432 filed May 20, 2002, the process described above is followed for each of the imaging layers. Successive layers may be coated sequentially, in tandem, or in a combination of sequential and tandem coatings.

The compounds of the invention fall into a class commonly referred to as rhodols. They may be prepared by synthetic processes which are known to those skilled in the art, particularly in view of the state of the art and the specific preparatory examples provided below herein.

Typically, rhodol dyes are synthesized step-wise from cyclic anhydrides such as phthalic anhydride. Two pathways are available. In the first method, 3-dialkylaminophenols are reacted with phthalic anhydrides to afford 2-(4-dialkylamino-2-hydroxybenzoyl)benzoic acids, as described by Zink in U.S. Pat. No. 5,395,948 and Hatano in The Chemistry of Fluoran Leuco Dyes, R. Muthyala (ed.), p. 182–185. The substituted benzoic acids are then condensed with resorcinol derivatives in strong acids such as 98% sulfuric acid to provide rhodols (3'-hydroxy-6-aminofluorans) substituted with a 6'-dialkylamino group. The use of 3-arylaminophenols with phthalic anhydrides is a poor reaction. Consequently, rhodols substituted with a 6'-arylamino group are rare.

The second method for making rhodols is preferred for the synthesis of the novel compounds of the present invention. A variety of resorcinol derivatives are caused to react with various phthalic anhydride derivatives using aluminum chloride as catalyst to produce a 2-(2,4-dihydroxy)benzoyl benzoic acids in excellent yields. The 2-(2,4-dihydroxy)benzoyl benzoic acids are condensed with some difficulty with a wide variety of 3-hydroxydiphenylamine derivatives to produce the novel red- and magenta-colored rhodol compounds of the present. Although heating the ketoacids with 3-hydroxydiphenyl amines and 3-hydroxytriphenyl amines with methanesulfonic acid in acetic acid provides rhodols as shown in the synthesis of Compound 1, trifluoroacetic anhydride in trifluoroacetic acid at 100–150° C. is a preferred method as illustrated by the synthesis of Compounds 2–6.

A third method for synthesizing rhodols is exemplified by the synthesis of Compound 7. Fluorescein is converted in high yield into its methyl ester by heating in methanol with sulfuric acid. Reaction of the ester with p-toluenesulfonyl chloride provides the 6'-p-toluenesulfonate ester. Displacement of p-toluenesulfonic acid by indoline provides the 6'-indolino-3'-hydroxyfluoran as a magenta solid. German patents DE116415 and DE116057 also report the synthesis of rhodols by displacement of the tosylate of fluorescein with ethylamine and diethylamine.

EXAMPLES

The invention will now be described further in detail with respect to specific embodiments by way of examples, it being understood that these are intended to be illustrative only and the invention is not limited to the materials, amounts, procedures and process parameters, etc. recited therein. All parts and percentages recited are by weight unless otherwise specified.

Example 1

Synthesis of Intermediates Used in the Synthesis of the Dyes.

Step 1A. Synthesis of 2-(5-bromo-2,4-dihydroxybenzoyl)benzoic acid

Aluminum chloride (8.48 g, 64 mmol) was added to a stirred suspension of phthalic anhydride (2.36 g, 16 mmol) in tetrachloroethane (40 mL) under nitrogen. Nitromethane (6 mL) was added to dissolve the reactants. 4-Bromoresorcinol (3 g, 16 mmol) was added and the mixture continued to be stirred under nitrogen. The reaction was monitored by high performance liquid chromatography (HPLC) over a period of 2 hours. It was observed that the reaction had ceased within the first 30 minutes, with starting materials remaining.

The solution was diluted with ethyl acetate (150 mL) and washed with 1M hydrochloric acid (2×100 mL). The product was extracted from the organic layer into a saturated solution of sodium bicarbonate in water (200 mL). The basic aqueous phase was acidified with 3M hydrochloric acid to a pH of 5. The product was extracted from the aqueous phase into ethyl acetate (150 mL), washed with brine (2×100 mL), dried over magnesium sulfate and concentrated to give an orange oil which solidified upon standing. The solid was slurried in dichloromethane (20 mL) and filtered to give a mixture of the desired product and phthalic acid. Slurrying in water (20 mL) followed by filtration gave the desired product as a beige powder (1.72 g, 5.1 mmol, 32% yield).

Step 1B. Preparation of 2-(5'-hexyl-2',4'-dihydroxybenzoyl)-3,4,5,6-tetrachloroobenzoic acid Tetrachlorophthalic anhydride (141 g, 0.493 mol) and 1,1,2,2-tetrachloroethane (700 mL) were added to a 3L 3-neck flask fitted with a mechanical stirrer under an atmosphere of nitrogen. Aluminum chloride (140 g, 1.05 mol) was added to the stirred mixture followed by 4-hexylresorcinol (97 g, 0.5 mol). The mixture was stirred overnight and the dark brown solution was poured onto ice (3 kg) and concentrated hydrochloric acid (400 mL). The heterogeneous mixture was stirred for 30 minutes and the layers were allowed to separate. The water layer was decanted and the remaining material was diluted with hexane and filtered. The yellow solid was washed with methylene chloride and dried in vacuo at 40° C. to a constant weight. The product was obtained as a yellow solid (174 g, 0.362 mol, 74% yield).

Step 1C. Alkylation of 3-Methoxydiphenylamine: Preparation of N-(3-methyl-1-butyl)-3-methoxydiphenylamine
A 60% oil dispersion of NaH (43 g, 1.05 mol) in a 2L 3-neck flask equipped with a mechanical stirrer was washed three times with hexane (3×125 mL). After the last wash, dry dimethylformamide(600 mL) was added. Under a nitrogen atmosphere, 3-methoxy diphenylamine (140 g, 0.71 mol) was added portionwise over a 15-minute period. After the addition was complete, the mixture was stirred for 45 minutes. 1-Bromo-3-methylbutane (120 g, 100 mL, 0.8 mol) was added to the cooled flask over an hour and stirred overnight. Ice water (300 g) was added very carefully to the cooled reaction mixture. The mixture was extracted with hexane (2×). The hexane extracts were washed with water, dried over sodium sulfate, and evaporated to dryness. A quantitative yield (189 g, 0.71 mol) of product as a light yellow oil was obtained.

Step 1D Synthesis of N-(1-dodecyl)-3-methoxydiphenylamine
Hexane (125 mL) was added to a 60% oil dispersion of NaH (50 g, 1.25 mol) in a 3L 3-neck equipped with a mechanical stirrer. The mixture was stirred 5 minutes and stopped. After the NaH had settled out, the hexane was decanted. This procedure was repeated twice. After the last decantation, dry DMF (700 mL) was added. Under a nitrogen atmosphere, 3-methoxydiphenylamine (172.2 g, 0.864 mol) was added portionwise over a 15-minute period. After the addition was complete, the mixture was stirred for 45 minutes. 1-Bromododecane (236 g, 0.948 mol) was added to the cooled flask over 3.5 hours while maintaining the temperature below 45° C. After stirring an additional ½ hour the reaction was worked up by carefully adding ice water (400 g). The mixture was extracted with hexanes (2×800 mL). The hexane extracts were washed with water (2×), dried over sodium sulfate, and concentrated at reduced pressure on a rotary evaporator to a constant weight. The desired product was obtained as a mobile yellow oil in greater than quantitative yield: (332.1 g, 104% yield). This material was directly used in the next step.

Step 1E. Synthesis of N-(2-ethyl-1-hexyl)-3-methoxydiphenylamine
Potassium t-butoxide (7.6 g, 0.062 mol) was dissolved in dry dimethylformamide (50 mL) in a 250 mL 3-neck flask. To this solution was added 3-methoxydiphenylamine (9.95 g, 0.050 mol) and the solution turned dark. 1-Bromo-2-ethylhexane (12.0 g, 0.062 mol) was added and the reaction mixture was stirred overnight at ambient temperature. The reaction mixture was poured into water (100 mL) and extracted with hexanes (2×50 mL). The combined hexane fractions were washed with water, dried over sodium sulfate and concentrated to afford the N-dodecyl-3-methoxy diphenylamine as a red-orange oil. The oil was purified by silica gel chromatography (19:1 hexanes/ethyl acetate). The product was isolated as a near colorless liquid (12.5 g, 0.040 mol, 80% yield).

Step 1F. Synthesis of 3-methoxy-triphenylamine
A solution of 3-methoxydiphenylamine (199 g, 1.0 mol), iodobenzene (816 g, 4 mol), pyridine (79.1 g, 1 mol) and toluene (400 mL) was heated to 90–100° C. with mechanical stirring. To this was added cuprous bromide (71.7 g, 0.5 mol) and potassium hydroxide (448.9 g, 8 mol). The mixture was heated at boiling for 12 hours. The reaction mixture was cooled to room temperature and filtered to remove the solids. The clear filtrate was separated from the red solid which was triturated with toluene (2×200 mL). The toluene layer was combined with the clear filtrate, washed with 10% acetic acid, saturated sodium bicarbonate and brine. The toluene was removed and the iodobenzene was steam distilled. The residue was extracted with heptane (4×1L). The combined heptane extract was treated with neutral alumina (200 g) and filtered. After washing the alumina with heptane (4×500 mL) the combined heptane solutions were concentrated to afford a colorless oil which crystallized when seeded with crystalline product (240 g, 0.87 mol, 87% yield).

Step 1G. Synthesis of N-(3-methyl-1-butyl)-3-hydroxydiphenylamine
N-(3-methyl-1-butyl)-3-methoxydiphenylamine (189 g, 0.71 mol) was dissolved in methylene chloride (600 ml) in a 3L three-neck flask fitted with a thermometer, a dropping funnel, and a nitrogen inlet. Boron tribromide (100 g, 0.4 mol) was added dropwise to the solution at 0° C. After the addition was complete, the mixture was stirred at room temperature overnight. The blue green solution was cooled in ice and treated carefully with ice water (600 g). Solid sodium bicarbonate (80 g) was added very cautiously. The layers were separated and the aqueous layer was washed with methylene chloride. The methylene chloride extracts were combined, dried over sodium sulfate and evaporated to dryness. The product was obtained as a dark brown oil (176 g, 0.69 mol, 97% yield).

Step 1H. Synthesis of N-(2-ethyl-1-hexyl)-3-hydroxydiphenylamine
N-(2-ethyl-1-hexyl)-3-methoxydiphenylamine (11.25 g, 36.2 mol) was dissolved in methylene chloride (30 mL) and cooled with an ice bath. Boron tribromide (8.0 g, 32 mmol) was added dropwise over ½ hour. After stirring overnight at room temperature water (20 mL) was added followed by potassium hydroxide pellets (3 g). The methylene chloride layer was separated, washed with water, dried over sodium sulfate and concentrated. The crude product was purified by silica gel chromatography (19:1 hexanes/ethyl acetate) to afford the product as a nearly colorless oil (10 g, 33.7 mmol, 93% yield).

Step 1I Synthesis of N-dodecyl-3-hydroxydiphenylamine
Crude N-dodecyl-3-methoxydiphenylamine (332.1 g, 0.864 mol) was dissolved in methylene chloride (650 mL) in a 3L three-neck flask fitted with a thermometer, a dropping funnel, and a nitrogen inlet. Boron tribromide (125.7 g, 0.5 mol) was added dropwise to the solution cooled to 0° C. After addition was complete, the mixture was stirred at room temperature overnight. An aliquot showed no remaining starting material. The blue green solution was cooled in ice and treated carefully with ice water (1000 g). Sodium bicarbonate (78 g) was added in small portions very cautiously. The layers were separated and the aqueous layer was washed one time with with hexanes. The methylene chloride/hexane extracts were combined, dried over sodium sulfate, and concentrated at reduced pressure on a rotary evaporator to a constant weight. The product was obtained as a dark brown oil (314 g, 101% yield) and used directly in the next step.

Step 1J. Synthesis of 3-hydroxy-triphenylamine A boron tribromide (25 g, 100 mmol) solution in methylene chloride (50 mL) was added dropwise over 20 minutes to a solution of 3-methoxy-triphenylamine (9.3 g, 34 mmol) in methylene chloride (100 mL) cooled to 0° C. After the addition was complete the dark green mixture was further stirred at 0° C. for 2 hours. Water (120 mL) was then slowly added to the reaction. The organic layer was separated, washed with saturated sodium bicarbonate solution, dried over magnesium sulfate and concentrated. The crude product (8.7 g) was purified by silica gel chromatography (methylene chloride) to give the desired product as white solid: (7.3 g, 28 mmol, 83%). The structure was confirmed by proton and carbon NMR spectroscopy.

Example II
Synthesis of Compound I 2-(5-Bromo-2,4-dihydroxybenzoyl)benzoic acid (3.08 g, 9.14 mmol) and 3-hydroxydiphenylamine (1.69 g, 9.14 mmol) were dissolved in acetic acid (25 mL) and methane sulfonic acid (1.8 mL, 27.4 mmol) in a 100 mL flask. The reaction was heated at 100° for 7 hours. The reaction was allowed to cool to ambient temperature and remain overnight. The product crystallized from the reaction mixture. The product was collected, washed with acetic acid and acetone and vacuum dried to afford the desired dye as a dark red powder. (3.45 g, 6.95 mmol, 76% yield). The structure was confirmed by NMR and mass spectroscopy. HPLC analysis showed 96 Area % at 254 nm.

Example III
Synthesis of Compound II

N-Dodecyl-3-hydroxydiphenylamine (5.16 g, 0.014 mol), bromoketoacid (4.93 g, 0.014 mol), trifluoroacetic acid (25 mL) and trifluoroacetic anhydride (2.5 mL) were placed into a 100 mL pressure bottle. The mixture was heated with magnetic stirring at 110° C. for 7 hours. The reaction mixture was poured into ice-water (400 mL). The dark magenta solid was collected by suction filtration and washed with water. The crude solid was dissolved in ethyl acetate (400 mL) and washed with 2N sodium hydroxide. The organic layer was dried over sodium sulfate and concentrated. Silica gel chromatography (methanol/methylene chloride) afforded the dye as a red solid (4.1 g, 0.0063 mol, 45% yield).

Example IV
Synthesis of Compound III

3-Hydroxytriphenylamine (3.9 g, 15 mmol), 2-(4'-hexyl-2',4'-dihydroxy)benzoyl-3,4,5,6-tetrachlorobenzoic acid (7.2 g, 15 mmol), tetramethylenesulfone (30 mL) and trifluoroacetic anhydride (5.2 mL) were placed into a 100 mL pressure flask. The flask was sealed and heated at 160–165° C. for one hour. The mixture was cooled and poured into water. The semi-solid paste was collected and dissolved in ethyl acetate and washed with 3N sodium hydroxide. The solvent was removed and the residue redissolved in methylene chloride and extracted with 2N sodium hydroxide, washed with dilute hydrochloric acid, dried and concentrated. The product was purified by silica gel chromatography (methanol/methylene chloride) to afford a dark red solid (2.2 g, 3.1 mmol, 21% yield). Recrystallization from a small amount of hot acetone afforded pale pink crystals (1.35 g, 1.91 mmol, 13% yield).

Example V
Synthesis of Compound IV

N-(3-methylbutyl)-3-hydroxydiphenylamine (17.0 g, 0.067 mol), 2-(4'-hexyl-2',4'-dihydroxy)benzoyl-3,4,5,6-tetrachlorobenzoic acid (31.0 g, 0.065 mol), trifluoroacetic anhydride (21 mL, 0.15 mol) and tetramethylene sulfone (48 g) were added to a 250-ml medium pressure bottle. The flask was sealed with a teflon cap. The mixture was heated in an oil bath at 160° C. for 1.5 hours. The reaction mixture was poured into ice water (200 mL). The solution was neutralized with 2N sodium hydroxide. The isolated powder was washed with water (300 mL). The crude product was dissolved in ethyl acetate (400 mL) and was washed with 3N sodium hydroxide. The solvent was removed by rotary evaporation. The crude product was crystallized from methylene chloride/acetonitrile to yield red crystals (18 g, 25.7 mmol, 40% yield). The mother liquors were concentrated and purified by silica gel chromatography (2% methanol) to yield magenta powder (7.2 g, 10.3 mmol, 16% yield) to give a total yield of 25.2 g (36 mmol, 56% yield).

Example VI
Synthesis of Compound V

N-(dodecyl)-3-hydroxydiphenylamine (19.2 g, 0.054 mol), 2-(4'-hexyl-2',4'-dihydroxy)benzoyl-3,4,5,6-tetrachlorobenzoic acid (26.1 g, 0.054 mol), trifluoroacetic acid (100 mL) and trifluoroacetic anhydride (15 mL, 0.106 mol) were added to a 250-mL pressure bottle and the bottle sealed with a teflon cap. The mixture was heated in an oil bath at 150° C. for 1 hour. The reaction mixture was poured into ice water (800 g) and neutralized with sodium carbonate. The gummy solid was then dissolved in ethyl acetate (600 mL) and washed with 2M aqueous sodium hydroxide solution (300 mL). After drying over sodium sulfate the solvent was removed by rotary evaporation. The residue was purified by silica gel column chromatography (2–3% methanol/methylene chloride) to give the desired product (16.2 g, 0.020 mol, 38%) which was precipitated from a small volume of methylene chloride with hexanes as a red solid.

The structure was confirmed by NMR and mass spectroscopy.

Example VII
Synthesis of Compound VI

N-(2-ethyl-1-hexyl)-3-hydroxydiphenyl-amine (29.7 g, 100 mmol), 2-(5'-hexyl-2',4'-dihydroxybenzoyl)-3,4,5,6-tetrachloroobenzoic acid (48.0 g, 100 mmol), trifluroacetic anhydride (30 mL), and trifluoroacetic acid (50 mL) were placed in a 250 mL pressure bottle and the bottle was sealed and heated at 150–160° C. for 65 minutes. After cooling to room temperature the reaction mixture was poured onto ice (1000 g). The solid was collected and taken up in ethyl acetate (1L) and washed with 5% sodium hydroxide (2×100 mL) and 10% sodium hydroxide (100 mL). The organic layer was then washed with 1N hydrochloric acid (100 mL). The solvent was removed and the purple residue was purified by silica gel chromatography (0 to 4% methanol/methylene chloride). The pure fractions were combined and recrystallized from ethyl acetate/acetonitrile to give the desired product as a red solid (14 g, 19 mmol, 19% yield). The product was confirmed by NMR and mass spectroscopy.

Example VIII
Synthesis of Compound VII

Step 8A. Fluorescein (10 g; 30 mmol) was dispersed in methanol (30 mL) and concentrated sulfuric acid was added slowly. After the addition was complete the mixture was stirred with heating at 120° C. for 14 hours. After cooling the mixture, sodium bicarbonate was added to neutralize the mixture to give a solid. The crude product was filtered and washed with 2% sodium bicarbonate (200 mL), with water (4×) and with 1% acetic acid to give the fluorescein methyl ester (9.2 g, 26.4 mmol, 88.2% yield), m.p. 260–261° C.

Step 8B. The fluorescein methyl ester (8 g, 23.1 mmol) and potassium carbonate (9.6 g, 69.3 mmol) were dissolved in dimethylformamide (50 mL) at 90° C. and to the solution was added toluenesulfonyl chloride (6.6 g, 34.7 mmol) slowly for 30 minutes. The mixture was then further stirred with heating at 110° C. for 5 hours. The mixture, after being cooled to room temperature, was poured into water (1L) to give a precipitate which was collected by filtration and washed with water to give the product(10 g, 20 mmol, 86.5% yield).

Step 8c. The toluenesulfonyl fluorescein ester (2 g, 4 mmol) and indoline (1.4 g, 12 mmol) were dissolved in N-methylpyrrollidinone (100 mL) and the solution was stirred with heating at 95° C. for 17 hours. After being cooled to room temperature the mixture was poured into water (600 mL) to form a precipitate. The precipitate was filtered, washed with water and dried to give the ester (1.7 g, 3.9 mmol, 96.8% yield).

The desired dye was obtained by basic hydrolysis of the ester using the following method: the dye and aqueous sodium hydroxide (3 eq.) were dissolved in methanol and stirred with heating at 60° C. for 1 hour until TLC showed complete conversion. The crude product was purified by column chromatography (5% methanol in methylene chloride) to give the desired product. (1.35 g, 3.1 mmol, 78% yield)

The structure was confirmed by NMR and mass spectroscopy.

Although the invention has been described in detail with respect to various preferred embodiments, it is not intended to be limited thereto, but rather those skilled in the art will recognize that variations and modifications are possible which are within the spirit of the invention and the scope of the appended claims.

What is claimed is:

1. A compound represented by the formula

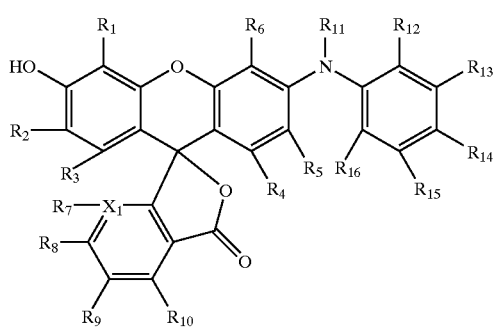

(I)

wherein:

$R_1$, $R_3$, $R_4$, $R_5$ and $R_6$ are each independently selected from the group consisting of hydrogen, alkyl, substituted alkyl, alkenyl, substituted alkenyl, alkynyl, substituted alkynyl, heterocycloalkyl, substituted heterocycloalkyl, substituted carbonyl, acylamino, halogen, nitro, nitrilo, sulfonyl, aryl, substituted aryl, heteroaryl, substituted heteroaryl, oxygen, substituted oxygen, nitrogen, substituted nitrogen, sulfur and substituted sulfur;

$R_2$ is selected from the group consisting of alkyl, substituted alkyl, alkenyl, substituted alkenyl, alkynyl, substituted alkynyl, heterocycloalkyl, substituted heterocycloalkyl, substituted carbonyl, halogen, nitro, nitrilo, sulfonyl, aryl, substituted aryl, heteroaryl, substituted heteroaryl, oxygen, substituted oxygen, sulfur and substituted sulfur;

$R_7$ is absent or selected from the group consisting of hydrogen, alkyl, substituted alkyl, alkenyl, substituted alkenyl, alkynyl, substituted alkynyl, heterocycloalkyl, substituted heterocycloalkyl, substituted carbonyl, acylamino, halogen, nitro, nitrilo, sulfonyl, aryl, substituted aryl, heteroaryl, substituted heteroaryl, oxygen, substituted oxygen, nitrogen, substituted nitrogen, sulfur and substituted sulfur;

$R_8$, $R_9$, $R_{10}$, $R_{13}$, $R_{14}$, $R_{15}$ and $R_{16}$ are each independently selected from the group consisting of hydrogen, alkyl, substituted alkyl, alkenyl, substituted alkenyl, alkynyl, substituted alkynyl, heterocycloalkyl, substituted heterocycloalkyl, substituted carbonyl, acylamino, halogen, nitro, nitrilo, sulfonyl, aryl, substituted aryl, heteroaryl, substituted heteroaryl, oxygen, substituted oxygen, nitrogen, substituted nitrogen, sulfur and substituted sulfur;

$R_{11}$ is selected from the group consisting of hydrogen, alkyl, substituted alkyl, alkenyl, substituted alkenyl, alkynyl, substituted alkynyl, heterocycloalkyl, substituted heterocycloalkyl, substituted carbonyl, sulfonyl, aryl, substituted aryl, heteroaryl, substituted heteroaryl, substituted oxygen and substituted nitrogen;

$R_{12}$ is selected from the group consisting of hydrogen, alkyl, substituted alkyl, alkenyl, substituted alkenyl, alkynyl, substituted alkynyl, heterocycloalkyl, substituted heterocycloalkyl, substituted carbonyl, acylamino, halogen, nitro, nitrilo, sulfonyl, aryl, substituted aryl, heteroaryl, substituted heteroaryl, oxygen, substituted oxygen, nitrogen, substituted nitrogen, sulfur and substituted sulfur;

or $R_{11}$ and $R_{12}$ taken together represent the carbon atoms necessary to form a 5 or 6 membered substituted or unsubstituted heterocycloalkyl or heteroaryl group; and $X_1$ is carbon or nitrogen.

2. A compound according to claim 1 wherein $R_2$ is an electron-withdrawing group, $R_{11}$ is selected from the group consisting of hydrogen, alkyl, substituted alkyl, and aryl, $R_1$, $R_3$, $R_4$, $R_5$, $R_6$, $R_7$, $R_8$, $R_9$, $R_{10}$ $R_{12}$, $R_{13}$, $R_{14}$, $R_{15}$ and $R_{16}$ are each hydrogen and $X_1$ is carbon.

3. A compound according to claim 1 wherein $R_2$ is alkyl, $R_7$, $R_8$, $R_9$ and $R_{10}$ are each halogen, $R_{11}$ is selected from the group consisting of hydrogen, alkyl, substituted alkyl, aryl and substituted aryl, $R_1$, $R_3$, $R_4$, $R_5$, $R_6$, $R_{12}$, $R_{13}$, $R_{14}$, $R_{15}$ and $R_{16}$ are each hydrogen and $X_1$ is carbon.

4. A compound according to claim 1 wherein $R_2$ is alkyl, $R_7$, $R_8$, $R_9$ and $R_{10}$ are each hydrogen or halogen, $R_1$, $R_3$, $R_4$, $R_5$, $R_6$, $R_{13}$, $R_{14}$, $R_{15}$ and $R_{16}$ are each hydrogen, $X_1$ is carbon, and $R_{11}$ and $R_{12}$, taken together, form a saturated ring.

* * * * *